United States Patent
Coupland

(10) Patent No.: US 6,956,059 B2
(45) Date of Patent: Oct. 18, 2005

(54) ANTI-INFLAMMATORY AND IMMUNOMODULATORY AMINO ACID DERIVATIVES, THEIR PREPARATION AND USE

(75) Inventor: Keith Coupland, Hotham (GB)

(73) Assignee: Croda International, plc, North Humberside (GB)

( * ) Notice: Subject to any disclaimer, the term of this patent is extended or adjusted under 35 U.S.C. 154(b) by 0 days.

(21) Appl. No.: 10/478,819

(22) PCT Filed: May 20, 2002

(86) PCT No.: PCT/GB02/02375

§ 371 (c)(1),
(2), (4) Date: Jun. 28, 2004

(87) PCT Pub. No.: WO02/094764

PCT Pub. Date: Nov. 28, 2002

(65) Prior Publication Data

US 2004/0242663 A1 Dec. 2, 2004

(30) Foreign Application Priority Data

May 21, 2001 (GB) .............................. 0112324

(51) Int. Cl.$^7$ .............................. A01M 37/18
(52) U.S. Cl. .................. 514/613; 514/627; 514/885; 514/886; 554/51; 554/58; 554/68; 554/69
(58) Field of Search .............................. 554/51, 58, 68, 554/69; 514/613, 627, 885, 886

(56) References Cited

FOREIGN PATENT DOCUMENTS

| GB | 2 357 083 A | 11/2000 |
|---|---|---|
| WO | 91/07955 | * 6/1991 |

* cited by examiner

Primary Examiner—Deborah D. Carr
(74) Attorney, Agent, or Firm—Robert D. Buyan; Stout, Uxa, Buyan & Mullins, LLP

(57) ABSTRACT

The present invention ralates to compounds of formula (I): wherein R is hydrogen (H) or $C_{1-6}$ alkyl; and X is defined such that —NH—(X)—COOH is the residue of an amino acid, which amino acid may itself optionally be substituted at any pendant amino group thereof by a residue of a carboxylic acid or a derivative thereof; or a salt thereof. The use of these compounds, in particular as potential anti-inflammatory and immunomodulatory drugs, and their preparation are described (I)

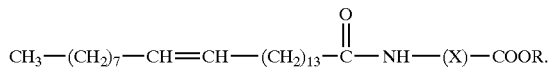

19 Claims, No Drawings

ANTI-INFLAMMATORY AND IMMUNOMODULATORY AMINO ACID DERIVATIVES, THEIR PREPARATION AND USE

The present invention relates to certain amino acid derivatives with fatty acids and their preparation, and to the use of such compounds or pharmaceutical formulations thereof in medicine in a mammal, including man, as, for example, anti-inflammatory or immunomodulatory agents.

Fatty acids are generally known to include the carboxylic acids that make up glycerides, such as triacylglycerols, the carboxylic esters comprised in the fat storage cells of plants and animals. Many such fatty acids are straight-chain compounds, having from three to eighteen carbon atoms ($C_3$–$C_{18}$); except for the $C_3$ and $C_5$ compounds, only acids containing an even number of carbon atoms are present in substantial amounts, due to their biosynthesis. There are both saturated and unsaturated fatty acids, such as the unsaturated $C_{18}$ oleic, α-linoleic and γ-linolenic (GLA) fatty acids, each having one, two and three carbon-carbon double bonds, respectively. Conventional notation therefore refers to these acids as 18:1, 18:2 and 18:3 fatty acids, respectively. The configuration about these double bonds is usually cis, which lowers the melting point of the corresponding fat (compared to the corresponding saturated and trans compounds).

Besides these short- and medium-chain fatty acids, those with longer chains, such as $C_{16}$–$C_{24}$, are also known and have been investigated, particularly those available from fish oils, such as eicosapentaenoic (EPA, 20:5 (n-3)) and docosahexaenoic (DHA, 22:6 (n-3)) acids, where, in (n-x), x indicates the position of the first carbon-carbon double bond with respect to the terminal methyl group on the fatty acid.

As well as their dietary metabolism and their potential dietary use, some fatty acids have been investigated in relation to medical conditions such as schizophrenia (GLA and DHA) and bipolar disorder (EPA and DHA). Some have also been proposed for improving the transport of biologically active drugs ('bioactives') across lipid membranes by linking the bioactive either directly or indirectly to certain fatty acids.

Some fatty acids have been proposed for use as general emulsifiers and surfactants when linked to an amino acid via the amino nitrogen atom. Such fatty acids include lauric (C12), myristic (C13), palmitic (C16), stearidonic (C18), linoleic (C18), arachidonic (C20) and behenic (C22) acids, and such amino acids include methionine, threonine, lysine, glycine, alanine and aspartic acids. The preparation of such fatty acid derivatives of amino acids is described by, for example, Paquet in Can J Biochem 58 573–6 (1980) and in Can J Chem 54 733–7 (1975).

However, no possibility of using other types of fatty acids, such as those having only one carbon-carbon double bond, or long chains, such as 24 carbon atoms, is contemplated in these references. One such different type of fatty acid is nervonic acid. Nervonic acid (24:1 (n-9)) is cis (or z)-tetracos-15-enoic acid; it is not classed as an essential fatty acid and has only one unsaturated C═C bond. It plays a part in the biosynthesis of myelin and is one of the major fatty acids in brain sphingolipids. Nervonic acid has therefore been implicated in diseases involving demyelination, such as adrenoleukodystrophy (ALD) and multiple sclerosis (MS). It has therefore been proposed to administer nervonic acid or a source thereof as a pharmaceutical formulation thereof to patients suffering from demyelinating conditions (as described in PCT published specification no. WO 91/07955), or to provide nervonic acid or a functional derivative thereof as a dietary supplement, for example, as baby or infant feeds, or to pregnant or lactating women (as described in PCT published specification no. PCT/GB95/01985).

Although the precise causes of MS are not yet known, strong evidence now suggests that MS results from an auto-immune process triggered by an environmental factor, possibly a non-specific viral infection, in a genetically susceptible individual, in which immune cells mistake myelin as a foreign invader and attack it. This process produces perivascular inflammation in the CNS and eventually damages not only myelin but also underlying nerve tissue. However, nervonic acid is not known to have any general effect on inflammation or inflammatory diseases.

As a result of damage to the myelin and nerve tissue, the blood-brain barrier is disrupted, enabling activated T-cells to enter the brain and recruit other lymphocytes. Activated T-cells release lymphotoxin, interferon gamma (IFN-γ) and other inflammatory cytokines. Lymphotoxin can damage oligodendrocytes, and IFN-γ, which has been shown to provoke MS exacerbations, stimulates the immune system in a number of ways thought to aggravate MS. Oligodendrocyte cells synthesise myelin-specific proteins and lipids, and their role is critical for both normal myelin sheath formation and normal brain function.

For example, IFN-γ augments expression of major histocompatibility complex (MHC) class II molecules on macrophages, and induces their expression on astrocytes, microglia and endothelial cells. Antigenic myelin peptides associated with these MHC molecules are recognised by T-cells, which proliferate in response to antigen presentation, amplifying the immune response.

Macrophages activated by IFN-γ also release tumour necrosis factor (TNF), which has been shown to damage oligodendrocytes in vitro. In addition, cytokines, proteinases and lipases are secreted, and B-cells are induced to synthesise antibodies. This response results in demyelination and gliosis, which causes nerve impulses to be slowed or halted and produces the symptoms of MS.

It has now surprisingly been found that certain amino acid derivatives of nervonic acid possess anti-inflammatory and/or immunomodulatory activity. Furthermore, some of these derivatives assist in the passage of nervonic acid across the blood-brain barrier.

Accordingly, the present invention provides a compound of formula (I):

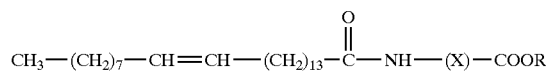

(I)

wherein R is hydrogen (H) or $C_{1-6}$ alkyl;
X is defined such that —NH—(X)—COOH is the residue of an amino acid, which amino acid may itself optionally be substituted at any pendant amino group thereof by a residue of a carboxylic acid or a derivative thereof;
or a salt thereof.

The definition of formula (I) also includes, where applicable, individual isomers and mixtures thereof.

By "derivatives" in the context of this invention is generally meant a product of a reaction between any reactive group of the compound referred to with a reactive group of a reactant. For example, the reactive group of the compound may be a carboxylic acid group. The reactive group of the reactant may be an alcohol or glycol —OH group (to form an ester) or the reactant may comprise an acyl donor such as an acid halide or anhydride. As well as such products, eg esters, "derivative" includes biopreursors or pro-drugs of the compounds of formula (I); and solvates (especially hydrates) thereof.

The term "bioprecursor" or "pro-drug" means a pharmacologically acceptable derivative—eg an ester (such as a biolabile ester derivative of a —COOH group)—that is converted in vivo to the compound of the present invention. "Bioprecursors" also include compounds in which the nervonic acid-derived component of the molecule (ie $CH_3$—$(CH_2)_7$—CH=CH—$(CH_2)_{13}$—C=O) is replaced by a component capable of conversion in vivo to nervonic acid, such as C22:1(n-9) and C26:1(n-9) fatty acids. Suitable pro-drugs can be determined by reference to Goodman and Gilman, The Pharmacological Basis of Therapeutics, 8th Edition, McGraw-Hill, Int. Ed. 1992, particularly "Biotransformation of Drugs", pp. 13–15.

Preferred salts of the compounds of formula (I) are those that are pharmacologically and/or pharmaceutically acceptable. In general, the pharmaceutically acceptable salts of the compounds of the formula (I) include suitable base salts thereof. Suitable pharmaceutical salts may be determined by reference to Berge et al, J Pharm Sci, 66, 1–19 (1977).

By way of example, suitable base salts are formed from organic and inorganic bases that form non-toxic salts. Examples thereof are the aluminium, calcium, lithium, magnesium, potassium, sodium, zinc, glucamine, amino acid residues, N-benzyl-N-(2-phenylethyl)amine, 1-adamantylamine and diethanolamine salts. Preferred base salts are the sodium, potassium, lithium, glucamine, N-benzyl-N-(2-phenylethyl)amine and 1-adamantylamine salts.

When R is $C_{1-8}$ alkyl, the alkyl group may be straight or branched chain and is preferably ethyl.

The amino acid from which —NH—(X)—COOR in formula (I) is derived may have one or more amino groups and must be physiologically acceptable. Hence, simple diamines such as 1,3-diamino alkanes are not suitable. Particularly suitable amino acids are those that have already been investigated or approved for food use and include those in which the 2-carbon atom (alpha to the —COOR group) is other than $CH_2$.

The carboxylic acid referred to in the definition of X preferably has from 1 to 26 carbon atoms, and may be straight- or branched-chain, saturated or unsaturated. More preferably, the carboxylic acid is straight chain and is selected from the group consisting of mono- and poly-unsaturated fatty acids. Particularly preferred are compounds of formula (I) wherein X is $R^1$—CH(Y)— in which $R^1$ is a covalent bond or an alkylene chain, preferably having from 1 to 4 carbon atoms in the chain; and Y is an alkylene chain, preferably having from 1 to 4 carbon atoms in the chain, any of which carbon atoms, together with the hydrogen atoms to which they are bonded, may be replaced by —O— or —S— (such as in methionine), or any of which hydrogen atoms may be substituted, such as by hydroxy (such as in threonine), or Y may be $NHR^2$ in which $R^2$ is H (such as in lysine) or a residue of a carboxylic acid or a derivative thereof, such as a $C_{18}$ to $C_{24}$ mono- or poly-unsaturated fatty acid, having from 1 to 6 carbon-carbon double bonds. Especially preferred is when $R^2$ is H or a residue of nervonic acid (24:1(n-9)) or docosahexaenoic acid (22:6(n-3)), where x in (n-x) indicates the position of the first double bond with respect to the terminal methyl group of the fatty acid.

The compounds of formula (I) may be prepared by any suitable method known to those skilled in the art, including and preferably in accordance with the methods described by Paquet (ibid). Preferred methods include:

(a) reaction of a reactive derivative of nervonic acid with $NH_2$—(X)—COOR or a salt thereof; and thereafter, optionally, if desired, (b) converting the compound of formula (I) so prepared to another compound of formula (I) by reaction thereof with a reactant to form a derivative thereof.

Especially preferred is when the reactive derivative of nervonic acid is the product of a reaction between nervonic acid and an acyl donor such as an acid halide or anhydride to form an acyl derivative, in particular the succinimidyl derivative. This can be prepared as described in Example 1 or by a suitable analogous method.

Accordingly, the invention provides a method wherein the compound of formula (I) is prepared by reaction of an acyl derivative, such as the succinimidyl derivative, of nervonic acid with $NH_2$—(X)—COOR or a salt thereof in the presence of a base.

Preferably, the conditions for the optional reaction (b) are those suitable for hydrolysis or further amine group substitution.

It will be understood by the person skilled in the art that the compounds of formula (I) wherein $R^2$ is H may also provide intermediates in the synthesis of other compounds of formula (I). Accordingly, the present invention provides a method for the preparation of the compounds of formula (I) wherein $R^2$ is a residue of a carboxylic acid, which method comprises reacting the corresponding compound of formula (IA):

(IA)

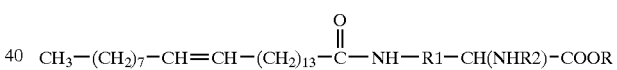

with the corresponding carboxylic acid of formula $R^2$—H or a reactive derivative thereof, wherein R, $R^1$ and $R^2$ are as defined for formula (I). Again, a preferred derivative is the succinimidyl derivative, especially that of a $C_{18}$ to $C_{24}$ mono- or poly-unsaturated fatty acid, having from 1 to 6 carbon-carbon double bonds.

Furthermore, compounds of formula (I) in which R is H may be esterified to provide the corresponding compounds in which R is $C_{1-6}$ alkyl, or vice versa.

Nervonic acid is commercially-available from Aldrich Chemicals, UK or is otherwise available as described, for example, in U.S. Pat. No. 5,194,448 or published PCT patent specification no. PCT/GB95/01985.

The compounds of formula (I) have, as mentioned before, surprisingly been found to possess anti-inflammatory and/or immunomodulatory activity.

Accordingly, the present invention provides the following specific compounds of formula (I):

N_ε-(z-15-tetracosenoyl)-L-lysine

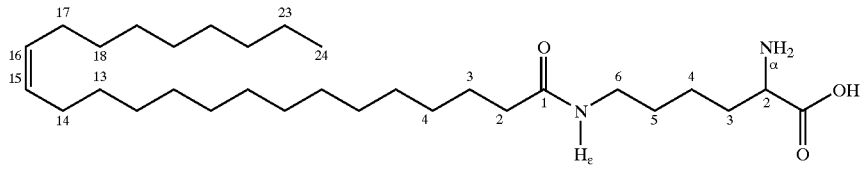

N_α,N_ε-di-(z-15-tetracosenoyl)-L-lysine ethyl ester

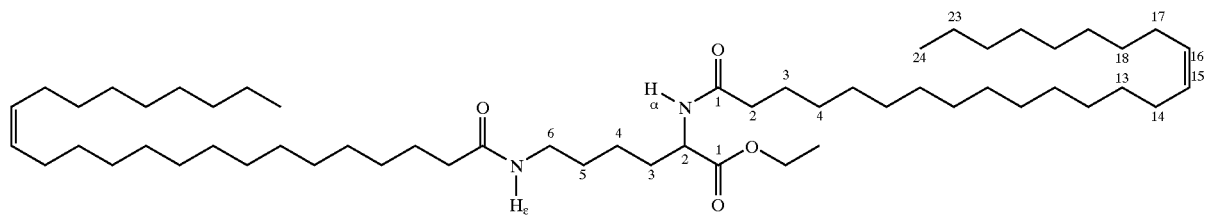

N_α,N_ε-di-(z-15-tetracosenoyl)-L-lysine

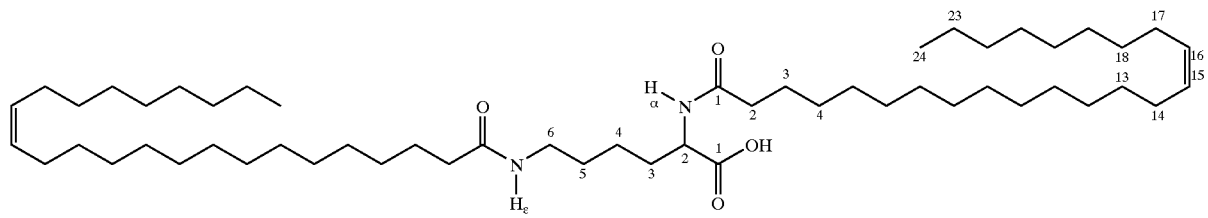

N-(z-15-tetracosenoyl)-L-methionine

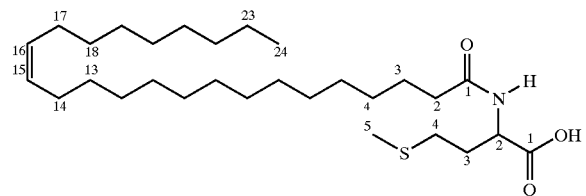

and
N-(z-15-tetracosenoyl)-L-threonine

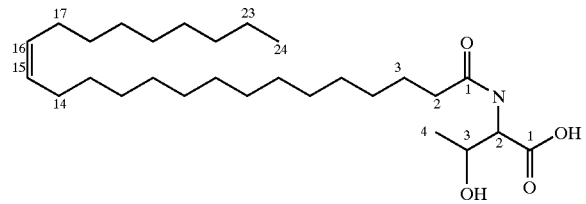

By 'anti-inflammatory' herein is meant the ability to reduce, ameliorate or prevent inflammation or an inflammatory response. By 'immunomodulatory' herein is meant the ability to modulate an immune response, such as by suppressing or stimulating such a response. It will be understood by those skilled in the art that both anti-inflammatory and immunomodulatory activity may be desirable for the treatment or prevention of some medical conditions.

Accordingly, the compounds of formula (I) may be used in the relief of rheumatoid arthritis, rheumatoid spondylitis, osteroarthritis, gouty arthritis and other arthritic conditions; inflamed joints; eczema and other inflammatory skin conditions; inflammatory eye conditions including conjunctivitis; pyresis and other conditions associated with inflammation, including the reduction of tissue necrosis in chronic inflammation, the suppression of tissue rejection following transplant surgery, Crohn's disease and ulcerative colitis.

The compounds of formula (I) may also be used in the treatment or prophylaxis of airway inflammatory conditions such as asthma and bronchitis. Other conditions, which are suitable for treatment by an immunomodulator, include systemic lupus erythematosis; multiple sclerosis; myasthenia gravis; progressive systemic sclerosis; atopic dermatitis; hyperimmunoglobin E; hepatitis B antigen negative chronic active hepatitis; Hashimoto's thyroiditis; familial Mediterranean fever; Grave's disease; autoimmune haemolytic anaemia; primary biliary cirrhosis; and inflammatory bowel disease. Further conditions, suitable for treatment by an immunostimulant, include any wherein the immune system is compromised, disabled or dysfunctional, such as in AIDS patients, and those associated with viral infections, such as HIV.

The amount required of a compound of formula (I) (the active ingredient) for therapeutic effect will, of course, vary both with the particular compound, the route of administration and the mammal under treatment. A suitable dose of a compound of formula (I) for a mammal suffering from a condition as defined hereinbefore is in the range of from 0.1 to 1000 mg of base per kilogram body weight, the most preferred dosage being 0.5 to 500 mg/kg of mammal body weight, such as from 1 to 50 mg/kg, for example 5 to 25 mg/kg; administered two or three times daily.

In the case of the treatment or prophylaxis of inflammatory airway conditions, a suitable anti-asthmatic dose of a compound of formula (I) is 1 mg to 10 mg of base per kilogram body weight, the most preferred dosage being 1 mg to 5 mg/kg of mammal body weight, for example from 1 to 2 mg/kg.

While it is possible for an active ingredient to be administered alone as the raw chemical, it is preferable to present it as a pharmaceutical formulation. The formulations, both for veterinary and for human medical use, of the present invention comprise an active ingredient in association with a pharmaceutically acceptable carrier therefor and optionally other therapeutic ingredient(s). The carrier(s) must be 'acceptable' in the sense of being compatible with the other ingredients of the formulation and not deleterious to the recipient thereof.

Conveniently, the active ingredient comprises from 0.1% to 99.9% by weight of the formulation. Conveniently, unit doses of a formulation contain between 0.1 mg and 1 g of the active ingredient. Preferably, the formulation is suitable for administration from one to six, such as two to four, times per day. For topical administration, the active ingredient preferably comprises from 1% to 2% by weight of the formulation but the active ingredient may comprise as much as 10% w/w. Formulations suitable for nasal or buccal administration, such as the self-propelling powder-dispensing formulations described hereinafter, may comprise 0.1 to 20% w/w, for example about 2% w/w of active ingredient.

The formulations include those in a form suitable for oral, ophthalmic, rectal, parenteral (including subcutaneous, vaginal, intraperitoneal, intramuscular and intravenous), intra-articular, topical, nasal or buccal administration.

The formulations may conveniently be presented in unit dosage form and may be prepared by any of the methods well known in the art of pharmacy. All methods include the step of bringing the active ingredient into association with the carrier, which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

Formulations of the present invention suitable for oral administration may be in the form of discrete units such as capsules, cachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion. The active ingredient may also be in the form of a bolus, electuary or paste. For such formulations, a range of dilutions of the active ingredient in the vehicle is suitable, such as from 1% to 99%, preferably 5% to 50% and more preferably 10% to 25% dilution. Depending upon the level of dilution, the formulation will be either a liquid at room temperature (in the region of about 20° C.) or a low-melting solid.

A tablet may be made by compressing or moulding the active ingredient optionally with one or more accessory ingredients. Compressed tablets may be prepared by compressing, in a suitable machine, the active ingredient in a free-flowing form such as a powder or granules, optionally mixed with a binder, lubricant, inert diluent, surface active or dispersing agent. Moulded tablets may be made by moulding, in a suitable machine, a mixture of the powdered active ingredient and a suitable carrier moistened with an inert diluent.

Formulations for rectal administration may be in the form of a suppository incorporating the active ingredient and a carrier such as cocoa butter, or in the form of an enema.

Formulations suitable for parenteral administration comprise a solution, suspension or emulsion, as described above, conveniently a sterile aqueous preparation of the active ingredient that is preferably isotonic with the blood of the recipient.

Formulations suitable for intra-articular administration may be in the form of a sterile aqueous preparation of the active ingredient, which may be in a microcrystalline form, for example, in the form of an aqueous microcrystalline suspension or as a micellar dispersion or suspension. Liposomal formulations or biodegradable polymer systems may also be used to present the active ingredient particularly for both intra-articular and ophthalmic administration.

Formulations suitable for topical administration include liquid or semi-liquid preparations such as liniments, lotions or applications; oil-in-water or water-in-oil emulsions such as creams, ointments or pastes; or solutions or suspensions such as drops. For example, for ophthalmic administration, the active ingredient may be presented in the form of aqueous eye drops, as for example, a 0.1–1.0% solution.

Drops according to the present invention may comprise sterile aqueous or oily solutions and may be prepared by dissolving the active ingredient in a suitable aqueous solution containing a bactericide and/or fungicidal agent and/or any other suitable preservative. The resulting solution may then be clarified by filtration, transferred to a suitable container, and then sealed and sterilised by autoclaving or maintaining at 90–100° C. for half an hour. The solution may be sterilised by filtration and transferred to the container by an aseptic technique. Preservatives, bactericidal and fungicidal agents suitable for inclusion in the drops are phenylmercuric salts (0.002%), benzalkonium chloride (0.01%) and chlorhexidine acetate (0.01%). Suitable solvents for the preparation of an oily solution include glycerol, diluted alcohol and propylene glycol.

Lotions according to the present invention include those suitable for application to the eye. An eye lotion may comprise a sterile aqueous solution optionally containing a bactericide or preservative prepared by methods similar to those for the preparation of drops. Lotions or liniments for application to the skin may also include an agent to hasten drying and to cool the skin, such as an alcohol, or a softener or moisturiser such as glycerol or an oil such as castor oil or arachis oil.

Creams, ointments or pastes according to the present invention are semi-solid formulations of the active ingredient for external application. They may be made by mixing the active ingredient in granule or powdered form, alone or in solution or suspension in an aqueous or non-aqueous solution in suitable machinery, with a greasy or non-greasy basis. The basis may comprise one or more of a hard, soft or liquid paraffin, glycerol, beeswax, a metallic soap; a mucilage; an oil such as a vegetable oil, eg almond, corn, arachis, castor or olive oil; wool fat or its derivatives; or a fatty acid ester of a fatty acid together with an alcohol such as propylene glycol or macrogols. The formulation may also comprise a suitable surface-active agent, such as an anionic, cationic or non-ionic surfactant such as a glycol or polyoxyethylene derivatives thereof. Suspending agents such as natural gums may be incorporated, optionally with other inorganic materials, such as silicaceous silicas, and other ingredients such as lanolin.

Formulations suitable for administration to the nose or buccal cavity include those suitable for inhalation or insufflation, and include powder, self-propelling and spray formulations such as aerosols and atomisers. The formulations, when dispersed, preferably have a particle size in the range of 10 to 200μ.

Such formulations may be in the form of a finely comminuted powder for pulmonary administration from a powder inhalation device or self-propelling powder-dispensing formulations, where the active ingredient, as a finely comminuted powder, may comprise up to 99.9% w/w of the formulation. In the case of self-propelling solution and spray formulations, the effect may be achieved either by choice of a valve having the desired spray characteristics (ie being capable of producing a spray having the desired particle size) or by incorporating the active ingredient as a suspended powder of controlled particle size. Thus the formulation, instead of passing into the lungs, is largely retained in the nasal cavity. These self-propelling formulations may be either powder-dispensing formulations or formulations dispensing the active ingredient as droplets of a solution or suspension.

Self-propelling powder-dispensing formulations preferably comprise dispersed particles of solid active ingredient, and a liquid propellant having a boiling point of below 18° C. at atmospheric pressure. The liquid propellant may be any propellant known to be suitable for medicinal administration and may comprise one or more lower alkyl hydrocarbons or halogenated lower alkyl hydrocarbons or mixtures thereof; chlorinated and fluorinated lower alkyl hydrocarbons are especially preferred. Generally, the propellant constitutes 50 to 99.9% w/w of the formulation whilst the active ingredient constitutes 0.1 to 20% w/w. for example, about 2% w/w, of the formulation.

The pharmaceutically acceptable carder in such self-propelling formulations may include other constituents in addition to the propellant, in particular a surfactant or a solid diluent or both. Surfactants are desirable since they prevent agglomeration of the particles of active ingredient and maintain the active ingredient in suspension. Especially valuable are liquid non-ionic surfactants and solid anionic surfactants or mixtures thereof. Suitable liquid non-ionic surfactants are those having a hydrophile-lipophile balance (HLB, see Journal of the Society of Cosmetic Chemists Vol. 1 pp. 311–326 (1949)) of below 10, in particular esters and partial esters of fatty acids with aliphatic polyhydric alcohols, for instance, sorbitan mono-oleate and sorbitan trioleate, available commercially as 'Span 80' (Trade Name) and 'Span 85' (Trade Name), respectively. The liquid non-ionic surfactant may constitute from 0.01 up to 20% w/w of the formulation, though preferably it constitutes below 1% w/w of the formulation. Suitable solid anionic surfactants include alkali metal, ammonium and amine salts of dialkyl sulphosuccinate (where the alkyl groups have 4 to 12 carbon atoms) and alkyl benzene sulphonic acid (where the alkyl group has 8 to 14 carbon atoms). The solid anionic surfactants may constitute from 0.01 up to 20% w/w of the formulation, though preferably below 1% w/w of the composition. Solid diluents may be advantageously incorporated in such self-propelling formulations where the density of the active ingredient differs substantially from the density of the propellant; also, they help to maintain the active ingredient in suspension. The solid diluent is in the form of a fine powder, preferably having a particle size of the same order as that of the particles of the active ingredient. Suitable solid diluents include sodium chloride, sodium sulphate and sugars.

Formulations of the present invention may also be in the form of a self-propelling formulation wherein the active ingredient is present in solution. Such self-propelling formulations may comprise the active ingredient, propellant and co-solvent, and advantageously an antioxidant stabiliser. The propellant is one or more of these already cited above. Co-solvents are chosen for their solubility in the propellant, their ability to dissolve the active ingredient, and for their having the lowest boiling point consistent with these above-mentioned properties. Suitable co-solvents are lower alkyl alcohols and mixtures thereof. The co-solvent may constitute 5 to 40% w/w of the formulation, though preferably less than 20% w/w of the formulation. Antioxidant stabilisers may be incorporated in such solution-formulations to inhibit deterioration of the active ingredient and are conveniently alkali metal ascorbates or bisulphites. They are preferably present in an amount of up to 0.25% w/w of the formulation.

Such self-propelling formulations may be prepared by any method known in the art. For example, the active ingredient (either as particles as described hereinbefore in suspension in a suitable liquid or in up to 20% w/w solution in an acceptable co-solvent, as appropriate) is mixed with any other constituents of the pharmaceutically acceptable carrier. The resulting mixture is cooled, introduced into a suitable cooled container and propellant is added thereto in liquid form; and the container is sealed. Alternatively, such self-propelling formulations may be prepared by mixing the active ingredient either in particles as hereinbefore described or in 2 to 20% w/w alcohol or aqueous solution as appropriate, together with the remaining constituents of the pharmaceutically acceptable carrier other than the propellant; introducing the resulting mixture, optionally with some propellant, into a suitable container; and injecting the propellant, under pressure, into the container at ambient temperature through a valve which comprises a part of the container and is used to control release of the formulation from it. Desirably, the container is purged by removing air from it at a convenient stage in the preparation of the self-propelling formulation.

A suitable container for a self-propelling formulation is one provided with a manually operable valve and constructed of aluminium, stainless steel or reinforced glass. The valve should, of course, be one having the desired spray characteristics of particle that which delivers a fixed amount of the formulation on the occasion of each operation of the valve, for example, about 50 to 100 microliters of formulation in each delivery; metered-dose devices are well known to those skilled in the art.

Formulations of the present invention may also be in the form of an aqueous or dilute alcoholic solution, optionally a sterile solution, of the active ingredient for use in a nebuliser or atomiser, wherein an accelerated air stream is used to produce a fine mist consisting of small droplets of the solution. Such formulations usually contain a flavouring agent such as saccharin sodium and a volatile oil. A buffering agent such as sodium metabisulphite and a surface-active agent may also be included in such a formulation which should also contain a preservative such as methylhydroxybenzoate.

Other formulations suitable for nasal administration include a powder, having a particle size of 20 to 500 microns, which is administered in the manner in which snuff is taken, ie by rapid inhalation through the nasal passage from a container of the powder held close up to the nose.

In addition to the aforementioned ingredients, the formulations of this invention may include one or more additional ingredients such as diluents, buffers, flavouring agents, binders, surface active agents, thickeners, lubricants, preservatives eg methylhydroxybenzoate (including antioxidants), emulsifying agents and the like. A particularly preferred carrier or diluent for use in the formulations of this invention is a lower alkyl ester of a $C_{18}$ to $C_{24}$ monounsaturated fatty acid, such as oleic acid, for example ethyl oleate. Other suitable carriers or diluents include capric or caprylic esters or triglycerides, or mixtures thereof, such as those caprylic/capric triglycerides sold under the trade name Miglyol, eg Miglyol 810.

Any other therapeutic ingredient may comprise one or more of the following: antibiotic, antifungal and antiviral agents.

According to the present invention there are therefore provided:

(a) a novel compound of formula (I), including derivatives (eg bioprecursors or prodrugs) and solvates thereof, or a salt thereof;
(b) a method for preparing a compound of formula (I), such as by esterification or de-esterification of a compound (I) to prepare another compound of formula (I); or by reacting the fatty acid, such as nervonic acid, with the amino acid under suitable conditions, such as those described by Paquet (ibid);
(c) a pharmaceutical formulation comprising a non-toxic, effective amount of a compound of formula (I) or a pharmaceutically acceptable salt thereof and a pharmaceutically acceptable carrier therefor;
(d) a method for preparing such formulations;
(e) a method for the prophylaxis or treatment of inflammation in a mammal, including man, comprising the administration to said mammal of a non-toxic, effective anti-inflammatory amount of a compound of formula (I);
(f) a method for the prophylaxis or treatment of immunoregulatory conditions in a mammal, including man, comprising the administration to said mammal of a non-toxic, effective immunomodulatory amount of a compound of formula (I);
(g) a compound of formula (I) for use in medicine or therapy, such as in the inhibition of inflammation and/or the modulation of the immunoregulatory system;
(h) the use of a compound of formula (I) in the preparation of a medicament, such as for the treatment or prophylaxis of inflammation and/or conditions associated with hyper- or hypostimulation of the immune system; and
(i) the use of a compound of formula (IA) in the preparation of another compound formula (I).

The following examples are provided by way of illustration of the present invention. In the following Descriptions and Examples, the structures of the final products were determined by $^1$H and $^{13}$C NMR spectroscopy, using a JEOL JNM-GX 270 spectrometer. $^1$H and $^{13}$C chemical shifts were measured for solutions in $CDCl_3$ relative to the solvent. $CDCl_3$ is deuterated chloroform, DMSO is dimethyl sulphoxide and TFA is trifluoroacetic acid. Ner refers to the tetracosenoyloxy chain, Lys to the L-lysine residue, Met to the L-methionine residue and Thr to the L-threonine residue. All temperatures indicated are in degrees Celsius.

EXAMPLE 1

Preparation of $N_\epsilon$-(z-15-tetracosenoyl)-L-lysine

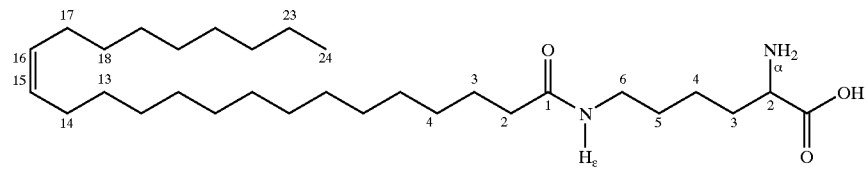

A. Preparation of Succinimidyl Nervonate

A solution of nervonoyl chloride (26 mmol, 10.0 g) in dichloromethane (50 mL) was added drop-wise to a cooled solution (0° C.) of N-hydroxysuccinimide (26 mmol, 3.0 g) and triethylamine (52 mmol, 5.2 g) in dicholoromethane (200 mL). The reaction was stirred for one hour after the addition was complete. TLC analysis (80:18:2 hexane-diethyl ether-acetic acid) indicated complete reaction. The reaction mixture was poured into hexane, filtered and concentrated to dryness. Recrystallisation from ethanol yielded succinimidyl nervonate as a white solid.

B. Preparation of $N_\epsilon$-(z-15-tetracosenoyl)-L-lysine

To a vigorously-stirred solution of L-lysine monohydrochloride (13 mmol, 2.4 g, commercially available) and triethylamine (39 mmol, 3.9 g) in 50 mL of water-acetone (1:1), was added succinimidyl nervonate (13 mmol, 6.0 g, prepared as in Example 1A) in portions during 0.5 h. During the addition, more water-acetone-triethylamine (10:10:2) was added in order to prevent the product from precipitating as a thick voluminous mass. Stirring was continued for an additional hour. The mixture was then acidified with hydrochloric acid in water (1:1, v/v) to pH 4 and chilled. The light foamy product was separated by filtration and washed with water and hot dioxane to yield the title compound.

ES-MS: (M+H) calcd. for $C_{30}H_{58}O_3N_2$ 495.4525, (M+H) obsvd. 495.4526.

$^1$H NMR: δ(DMSO/TFA): 0.81 (t, 3H, Ner H-24), 1.20 (m, 34H, Ner H-4-13, Ner H-18-23, Lys H-4), 1.33–1.80 (m, 6H, Ner H-3, Lys H-3,5), 1.94 (m, 4H, Ner H-14,17), 2.02 (t, 2H, Ner H-2), 3.00 (t, 2H, Lys H-6), 3.85 (m, 1H, Lys H-2), 5.28 (m, 2H, Ner H-15,16), 7.78 (t, 1H, $J_{N-H}$=5.6 Hz, Lys $NH_\epsilon$), 8.24 (dxd, 1H, $J_{N-H}$=4.6 Hz, Lys $NH_\alpha$).

$^{13}$C NMR: δ($CDCl_3$/TFA): 14.0 (Ner C-24), 22.8 (Ner C-23), 35.0 (Ner C-2), 40.4 (Lys C-6), 53.6 (Lys C-2), 130.1 (Ner C-15,16), 172.4 (CO, Ner C-1), 179.3 (CO, Lys C-1).

EXAMPLE 2

Preparation of $N_\alpha,N_\epsilon$-di-(z-15-tetracosenoyl)-L-lysine ethyl ester

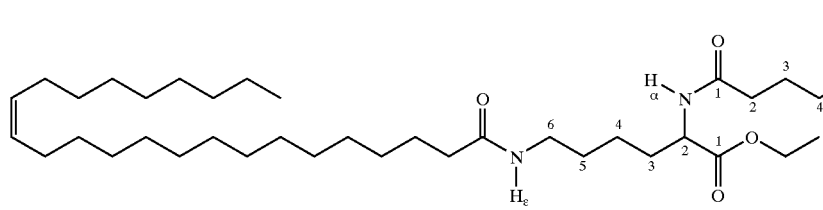

To a stirred suspension of L-lysine ethyl ester dihydrochloride (6 mmol, 1.4 g, commercially available) and triethylamine (36 mmol, 3.6 g) in chloroform (80 mL), succinimidyl nervonate (18 mmol, 8.4 g, prepared as described in Example 1) was added in portions at room temperature. Stirring was continued overnight and, after removal of the solvent under reduced pressure, the product was crystallised from ethanol:water (1:1), yielding the title compound.

IR (cm$^{-1}$): 1746, 1646, 1553. ES-MS: (M+H) calcd. for $C_{56}H_{106}O_4N_2$ 871.8231, (M+H) obsvd. 871.8244.

$^1$H NMR: δ(CDCl$_3$): 0.88 (t, 6H, Ner H-24, Ner' H-24), 1.28 (m, 69H, Ner H-4-13, Ner H-18-23, Ner' H-4-13, Ner' H-18-23, Lys H-4, Lys CH$_3$ ester), 1.48–1.88 (m, 8H, Ner H-3, Ner' H-3, Lys H-3,5), 2.01 (m, 8H, Ner H-14,17, Ner' H-14,17), 2.15 (t, 2H, Ner' H-2), 2.23 (t, 2H, Ner H-2), 3.22 (m, 2H, Lys H-6), 4.19 (q, 2H, Lys CH$_2$ ester), 4.55 (m, 1H, Lys H-2), 5.35 (m, 4H, Ner H-15,16, Ner' H-15,16), 5.78 (t, 1H, $J_{N-H}$=5.6 Hz, Lys NH$_\epsilon$), 6.23 (d, 1H, $J_{N-H}$=7.6 Hz, Lys NH$_\alpha$).

$^{13}$C NMR: δ(CDCl$_3$): 14.1 (Ner C-24, Ner' C-24), 22.3, 22.6 (Ner C-23, Ner' C-23), 36.5, 36.8 (Ner C-2, Ner' C-2), 38.7 (Lys C-5), 51.6 (Lys C-6), 61.4 (Lys C-2), 129.9 (Ner C-15,16, Ner' C-15,16), 172.6, 173.2, 173.4 (CO, Ner C-1, Ner' C-1, Lys C-1).

EXAMPLE 3

Preparation of $N_\alpha,N_\epsilon$-di-(z-15-tetracosenoyl)-L-lysine

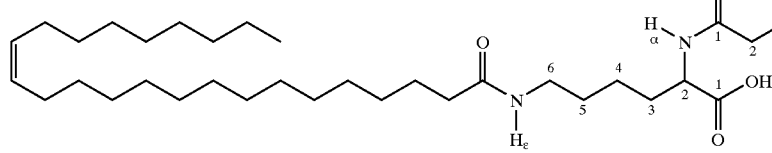

$N_\alpha,N_\epsilon$-di-(z-15-tetracosenoyl)-L-lysine ethyl ester (2 mmol, 1.74 g, prepared according to Example 2) was heated to gentle reflux with 3% methanolic sodium hydroxide solution (25 mL) for 2 hours and left at room temperature overnight. The soapy material was acidified to pH 2 with 1 N cold hydrochloric acid and the white solid was collected and recrystallised from acetone-water (1:1) giving the free acid title compound as a white powder.

IR (cm$^{-1}$): 1717, 1645, 1558. ES-MS: (M+H) calcd. for $C_{54}H_{102}O_4N_2$ 841.7762, (M+H) obsvd. 841.7750.

$^1$H NMR: δ(CDCl$_3$): 0.88 (t, 6H, Ner H-24, Ner' H-24), 1.27 (m, 66H, Ner H-4-13, Ner H-18-23, Ner' H-4-13, Ner' H-18-23, Lys H-4), 1.50–1.94 (m, 8H, Ner H-3, Ner' H-3, Lys H-3,5), 2.01 (m, 8H, Ner H-14,17, Ner' H-14,17), 2.19 (t, 2H, Ner' H-2), 2.26 (t, 2H, Ner H-2), 3.27 (m, 2H, Lys H-6), 4.54 (m, 1H, Lys H-2), 5.35 (m, 4H, Ner H-15,16, Ner' H-15,16), 5.94 (t, 1H, $J_{N-H}$=5.9 Hz, Lys NH$_\epsilon$), 6.67 (d, 1H, $J_{N-H}$=6.9 Hz, Lys-NH$_\alpha$).

$^{13}$C NMR: δ(CDCl$_3$): 14.1 (Ner C-24, Ner' C-24), 22.7 (Ner C-23, Ner' C-23), 36.4, 36.8 (Ner C-2, Ner' C-2), 38.7 (Lys C-5), 52.2 (Lys C-6), 129.9 (Ner C-15,16, Ner' C-15,16), 174.2, 174.5 (CO, Ner C-1, Ner' C-1, Lys C-1).

EXAMPLE 4

Preparation of N-(z-15-tetracosenoyl)-L-methionine

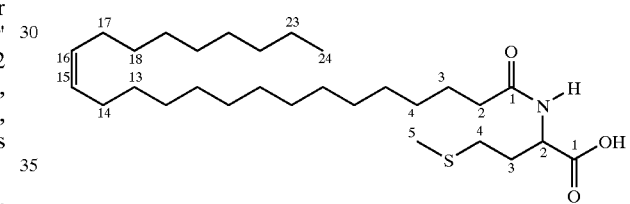

To a stirred solution of L-methionine (5 mmol, 0.75 g) and triethylamine (15 mmol, 2.1 mL) in 15 mL of water-acetone (1:1), was added succinimidyl nervonate (5 mmol, 2.32 g, prepared according to Example 1A) in portions. The mixture was stirred for 4 hours until no ester remained according to TLC (hexane-diethyl ether-acetic acid, 80:18:2). The solvents were evaporated under reduced pressure. 10 mL of water was then added and the mixture was acidified with concentrated hydrochloric acid to pH 2. The precipitated product was separated by filtration, washed with water and crystallised from ethanol. Hexane was then used to remove traces of non-polar impurities from the title compound.

IR (cm$^{-1}$): 1722, 1647, 1534. ES-MS: (M+H) calcd. for $C_{29}H_{55}O_3NS$ 498.3981, (M+H) obsvd. 498.3981.

$^1$H NMR: δ(DMSO): 0.81 (t, 3H, Ner H-24), 1.20 (m, 32H, Ner H-4-13, Ner H-18-23), 1.45 (m, 2H, Ner H-3), 1.81 (m, 2H, Met H-3), 1.93 (q, 4H, Ner H-14,17), 1.99 (s,

3H, Met H-5), 2.07 (m, 2H, Ner H-2), 2.42 (m, 2H, Met H-4), 4.25 (m, 1H, Met H-2), 5.25 (t, 2H, Ner H-15,16), 7.96 (d, 1H, $J_{N-H}$=8.0 Hz).

$^{13}$C NMR: δ(DMSO): 13.8 (Ner C-24), 14.6 (Met C-5), 35.2 (Ner C-2), 45.2 (Met C-3), 51.2 (Met C-2), 129.3, 129.4 (Ner C-15,16), 172.1, 173.7 (C=O, Ner C-1, Met C-1).

EXAMPLE 5

Preparation of N-(z-15-tetracosenoyl)-L-threonine

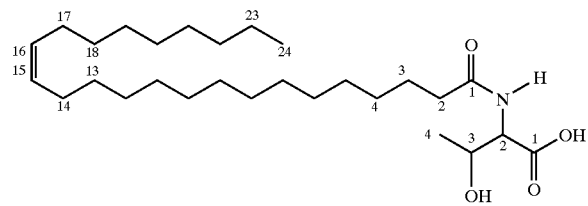

A mixture of L-threonine (5 mmol, 0.595 g), sodium bicarbonate (5 mmol, 0.420 g) and succinimidyl nervonate (5 mmol, 2.320 g, prepared according to Example 1A) in water (2 mL) and dimethoxyethane (5 mL) were refluxed for 2 hours until no ester remained according to TLC (hexane-diethyl ether-acetic acid, 80:18:2). Acidification to pH 2 with concentrated hydrochloric acid and chilling gave the title product, which was washed with water, dried and crystallised from chloroform. It was finally washed with hexane to remove small amounts of non-polar contaminants.

IR (cm$^{-1}$): 1717, 1647, 1542. ES-MS: (M+H) calcd. for $C_{28}H_{53}O_4N$ 468.4053, (M+H) obsvd. 468.4053.

$^1$H NMR: δ(DMSO): 0.82 (t, 3H, Ner H-24), 1.01 (d, 3H, J=6.8 Hz, Thr H-4), 1.20 (m, 32H, Ner H-4-13, 18-23), 1.46 (m, 2H, Ner H-3), 1.94 (q, 4H, Ner H-14,17), 2.15 (m, 2H, Ner H-2), 4.09 (m, 1H, J=6.8 Hz, Thr H-3), 4.19 (dxd, 1H, J=8.7 Hz, Thr H-2), 5.27 (t, 2H, Ner H-15,16), 7.66 (d, 1H, $J_{N-H}$=8.7 Hz).

$^{13}$C NMR: δ(DMSO): 13.8 (Ner C-24), 20.3 (Thr C-4), 35.2 (Ner C-2), 57.5 (Thr C-3), 66.4 (Thr C-2), 129.4, 129.5 (Ner C-15,16), 172.4, 172.6 (C=O, Ner C-1, Thr C-1).

EXAMPLE A

Tablet

| In one tablet | |
|---|---|
| Active ingredient | 5.0 mg |
| Lactose | 82.0 mg |
| Starch | 10.0 mg |
| Povidone | 2.0 mg |
| Magnesium stearate | 1.0 mg |

The active ingredient, lactose and starch, are mixed together. The powders are granulated using a solution of povidone in purified water. The granules are dried, the magnesium stearate added and the mixture compressed to produce tablets, 100 mg per tablet.

EXAMPLE B

Ointment Composition

| Active ingredient | 1.0 mg |
|---|---|
| White soft paraffin | to 100.0 g |

The active ingredient is dispersed in a small volume of the vehicle and then incorporated into the bulk of the vehicle to produce a smooth, homogeneous product. Collapsile metal tubes are then filled with the dispersion.

EXAMPLE C

Topical Cream Composition

| Active ingredient | 1.0 g |
|---|---|
| Polawax GP 200 | 20.0 g |
| Lanolin Anhydrous | 2.0 g |
| White Beeswax | 2.5 g |
| Methyl hydroxybenzoate | 0.1 g |
| Distilled Water | to 100.0 g |

The polawax, beeswax and lanolin are heated together at 60° C. A solution of methyl hydroxybenzoate is added and homogenisation is achieved using high speed stirring. The temperature is reduced to 50° C. The active ingredient is then added and dispersed. The composition is allowed to cool with slow-speed stirring.

EXAMPLE D

Topical Lotion Composition

| Active ingredient | 1.0 g |
|---|---|
| Sorbitan monolaurate | 0.6 g |
| Polysorbate 20 ™ | 0.6 g |
| Cetostearyl alcohol | 1.2 g |
| Glycerin | 8.0 g |
| Methyl hydroxybenzoate | 0.2 g |
| Purified water B.P. | to 100.00 ml |

The methyl hydroxybenzoate and glycerin are dissolved in 70 ml of the water at 75°. The sorbitan monolaurate, Polysorbate 20™ and cetostearyl alcohol are melted together at 75° and added to the aqueous solution. The resulting emulsion is homogenised, allowed to cool with continuous stirring and the active ingredient is added as a suspension in the remaining water. The suspension is stirred until homogenised.

EXAMPLE E

Capsule Composition

A capsule is prepared by filling a two-piece hard gelatin capsule with 50 mg of active ingredient, 110 mg of lactose, 32 mg of talc and 8 mg of magnesium stearate.

EXAMPLE F

Eye Drop Composition

| | |
|---|---|
| Active ingredient | 0.5 g |
| Methyl hydroxybenzoate | 0.01 g |
| Propyl hydroxybenzoate | 0.04 g |
| Purified water B.P. | to 100.00 ml |

The methyl and propyl hydroxybenzoates are dissolved in 70 ml purified water and the resulting solution is allowed to cool. The active ingredient is added and the solution is sterilised by filtration through a membrane filter (0.22 μm pore size) and packed into suitable sterile containers.

EXAMPLE G

Composition for Administration by Inhalation

For an aerosol container with a capacity of 15–20 ml: active ingredient (10 mg) is mixed with 0.2–0.2% of a lubricating agent, such as Polysorbate 85™ or oleic acid or a mixture thereof, in a propellant, such as Freon™, preferably in a combination of 1,2-dichloroethene and difluorochloromethane, and the mixture is put into an appropriate aerosol container adapted for inhalation administration.

EXAMPLE H

Composition for Administration by Inhalation (Alcoholic Solution)

For an aerosol container with a capacity of 15–20 ml: active ingredient (10 mg) is dissolved in ethanol (6–8 ml), 0.1–0.2% of a lubricating agent is added, such as Polysorbate 85™, and dispersed in a propellant, such as Freon™, preferably in a combination of 1,2-dichloroethene and difluorochloramethane, and the mixture is put into an appropriate aerosol container adapted for nasal or oral inhalation administration.

EXAMPLE I

Injectable Parenteral Composition

An injection is prepared by stirring 1.5% by weight of active ingredient in propylene glycol and water. The solution is sterilised by filtration.

EXAMPLE J

Oral Composition

An oral composition is prepared by mixing 10 parts of active ingredient (NA:NA and/or NA:GLA) with 90 parts of ethyl oleate, resulting in 10% dilution of the lipid in ethyl oleate.

EXAMPLE K

Biological Data

In accordance with the methodology described by Dehouck et al in J Cont Rel 81–91 (1992), experiments were performed to study the transport of the compound of Example 2 across the blood-brain barrier. These results indicate that the compound is not cytotoxic when used at the concentration of 5 μm/l.

What is claimed is:
1. A compound of formula (I):

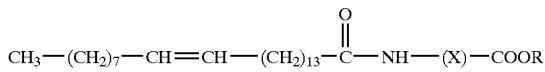

(I)

wherein R is hydrogen (H) or $C_{1-6}$ alkyl; and

X is defined such that —NH—(X)—COOH is the residue of an amino acid, which amino acid may itself optionally be substituted at any pendant amino group thereof by a residue of a carboxylic acid or a derivative thereof;

or a salt thereof.

2. A compound according to claim 1, wherein R is ethyl.

3. A compound according to claim 1, wherein the amino acid from which —NH—(X)—COOR in formula (I) is derived comprises one or more amino groups; is physiologically acceptable: and in which the carbon atom that is alpha to the COOR group is other than $CH_2$.

4. A compound according to claim 1, wherein the carboxylic acid referred to in the definition of X has from 1 to 26 carbon atoms, and is selected from mono- and poly-unsaturated fatty acids.

5. A compound according to claim 1, wherein X is R1-CH(Y)— in which R1 is a covalent bond or an alkylene chain, preferably having from 1 to 4 carbon atoms in the chain; and Y is an alkylene chain, preferably having from 1 to 4 carbon atoms in the chain, any of which carbon atoms, together with the hydrogen atoms to which they are bonded, may be replaced by —O— or —S— (such as in methionine), or any of which hydrogen atoms may be substituted, such as by hydroxy (such as in threonine), or Y may be NHR2 in which R2 is H (such as in lysine) or a residue of a carboxylic acid or a derivative thereof, such as a $C_{18}$ to $C_{24}$ mono- or poly-unsaturated fatty acid, having from 1 to 6 carbon-carbon double bonds.

6. A compound according to claim 5, wherein R2 is H or a residue of nervonic acid (24:1(n-9)) or docosahexaenoic acid (22:6(n-3)), where x in (n-x) indicates the position of the first double bond with respect to the terminal methyl group of the fatty acid.

7. A compound according to claim 1 that is selected from the group consisting of:

N-(z-15-tetracosenoyl)-L-lysine;

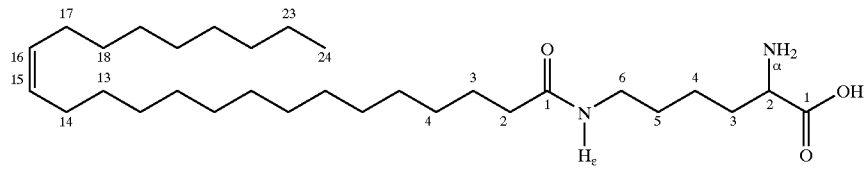

N,N-di-(z-15-tetracosenoyl)-L-lysine ethyl ester;

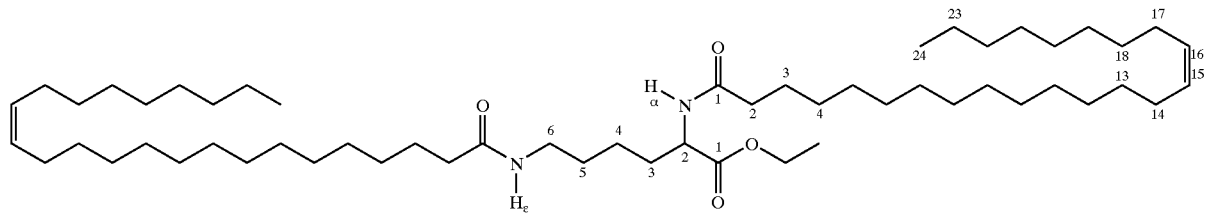

N,N-di-(z-15-tetracosenoyl)-L-lysine;

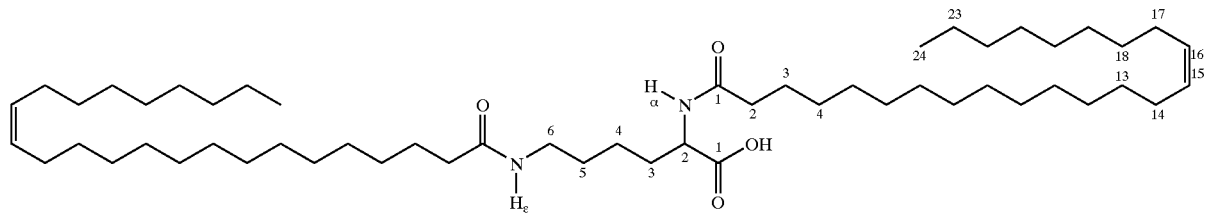

N-(z-15-tetracosenoyl)-L-methionine;

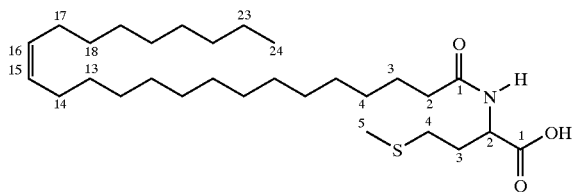

N-(z-15-tetracosenoyl)-L-threonine;

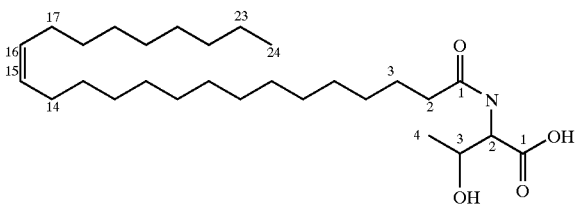

and salts thereof.

8. A method for the preparation of a compound of formula (I)

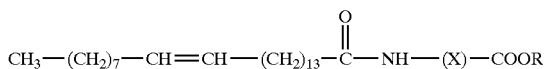

wherein R is hydrogen (H) or $C_{1-6}$ alkyl; and
X is defined such that —NH—(X)—COOH is the residue of an amino acid, which amino acid may itself optionally be substituted at any pendant amino group thereof by a residue of a carboxylic acid or a derivative thereof;
or a salt thereof,
said method comprising the step of:
(a) reacting a reactive derivative of nervonic acid with $NH_2$—(X)—COOR or a salt thereof.

9. A method according to claim 8 further comprising the optional step of:
(b) converting the compound of formula (I) to another compound of formula (I) or a salt thereof by reaction thereof with a reactant to form a derivative thereof.

10. A method according to claim 8, wherein the compound of formula (I) is prepared by reaction of the succinimidyl derivative of nervonic acid with $NH_2$—(X)—COOR or a salt thereof in the presence of a base.

11. A method according to claim 9, wherein conditions during performance of at least a portion of Step (b) are suitable for hydrolysis or further amine group substitution.

12. A compound according to claim 1 that is suitable for use in medicine.

13. A compound according to claim 12 that is suitable for administration to a human or veterinary patient in amounts that are effective to cause anti-inflammatory and/or immunomodulatory effects in the patient.

14. A compound according to claim 1 for use in the preparation of another compound according to claim 1.

15. A pharmaceutical composition comprising a non-toxic, effective amount of a pharmaceutically acceptable compound according to claim 1 in combination with a pharmaceutically acceptable carrier therefore.

16. A pharmaceutical composition according to claim 15 prepared by a method comprising the step of:
(a) bringing a compound according to claim 1 into association with a pharmaceutically acceptable carrier therefore.

17. A method for treating or preventing an inflammatory or autoimmune condition in a human or veterinary patient, said method comprising the steps of:
(a) providing a compound having general formula (I):

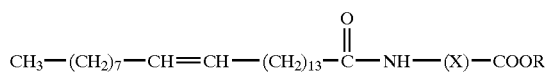

(I)

wherein R is hydrogen (H) or $C_{1-6}$ alkyl; and
X is defined such that —NH—(X)—COOH is the residue of an amino acid, which amino acid may itself optionally be substituted at any pendant amino group thereof by a residue of a carboxylic acid or a derivative thereof;

or a salt thereof; and (b) administering said compound to the patient in an amount that is substantially non-toxic and therapeutically effective to prevent or treat said condition.

18. A method according to claim 17 wherein the method is carried out to prevent or treat a condition selected from the group consisting of:

rheumatoid arthritis, rheumatoid spondylitis, osteroarthritis, gouty arthritis, arthritic conditions, inflamed joints, eczema, inflammatory skin conditions, inflammatory eye conditions, conjunctivitis, pyresis, tissue necrosis resulting from inflammation, tissue rejection following transplant surgery, Crohn's disease and ulcerative colitis, airway inflammation, asthma, bronchitis, systemic lupus erythematosis, multiple sclerosis, myasthenia gravis, progressive systemic sclerosis, atopic dermatitis, hyperimmunoglobin E, hepatitis B antigen negative chronic active hepatitis, Hashimoto's thyroiditis, familial Mediterranean fever, Grave's disease, autoimmune haemolytic anemia, primary biliary cirrhosis, inflammatory bowel disease, viral infections, HIV infections and AIDS.

19. A method according to claim 17 wherein the compound is selected from the group consisting of:

$N_\square$-(z-15-tetracosenoyl)-L-lysine;

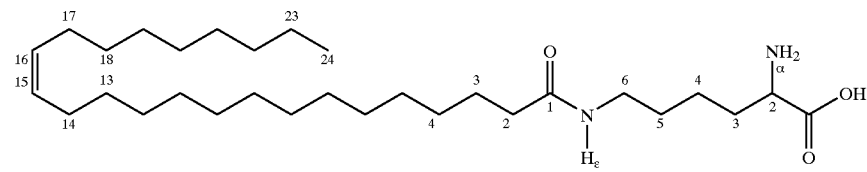

$N_\square,N_\square$-di-(z-15-tetracosenoyl)-L-lysine ethyl ester;

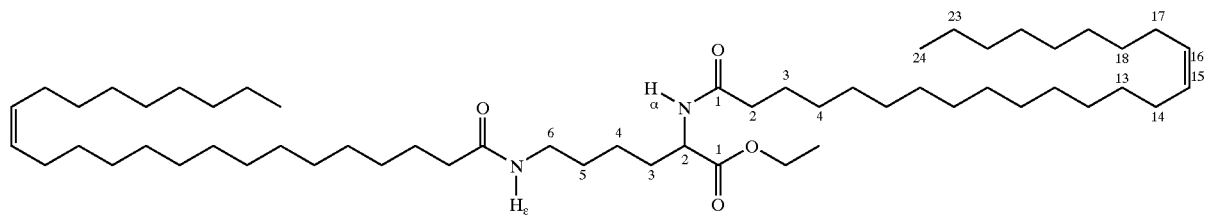

$N_\square,N_\square$-di-(z-15-tetracosenoyl)-L-lysine;

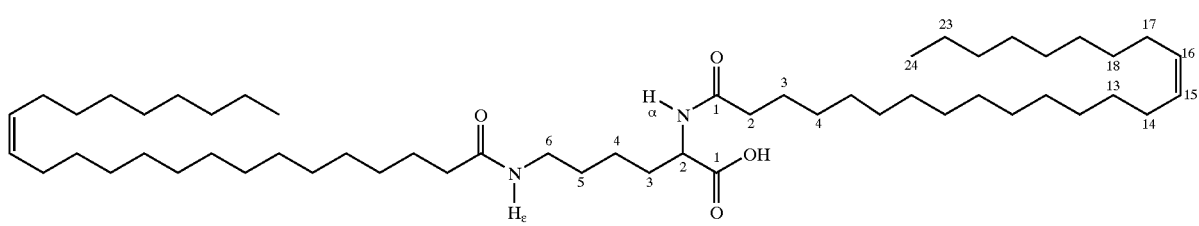

23
N-(z-15-tetracosenoyl)-L-methionine;
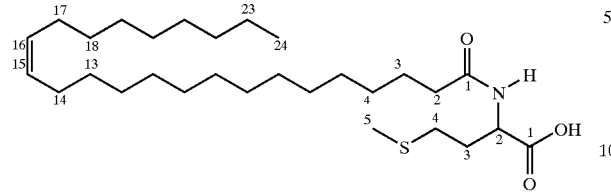
24
N-(z-15-tetracosenoyl)-L-threonine;
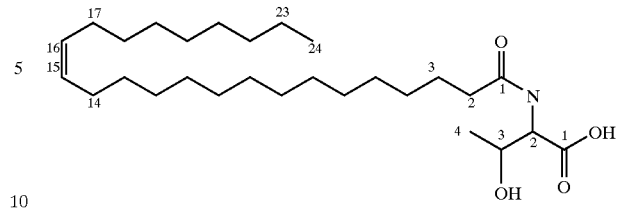
and salts thereof.
* * * * *